United States Patent
Goeggelmann et al.

(10) Patent No.: US 7,047,657 B2
(45) Date of Patent: May 23, 2006

(54) APPARATUS FOR RECORDING THE CONTOUR OF A SURFACE

(75) Inventors: Andreas Goeggelmann, Ingersheim (DE); Josef Kozak, Tuttlingen (DE)

(73) Assignee: Aesculap AG & Co. KG, Tuttlingen (DE)

(*) Notice: Subject to any disclaimer, the term of this patent is extended or adjusted under 35 U.S.C. 154(b) by 0 days.

(21) Appl. No.: 11/071,990

(22) Filed: Mar. 3, 2005

(65) Prior Publication Data

US 2005/0198849 A1   Sep. 15, 2005

Related U.S. Application Data

(63) Continuation of application No. PCT/EP2003/008856, filed on Aug. 8, 2003.

(30) Foreign Application Priority Data

Sep. 5, 2002  (DE) .............. 102 41 069

(51) Int. Cl.
*G01B 3/14* (2006.01)
(52) U.S. Cl. .............. 33/552; 33/551; 33/555
(58) Field of Classification Search .......... 33/549–561, 33/515
See application file for complete search history.

(56) References Cited

U.S. PATENT DOCUMENTS

| | | | | |
|---|---|---|---|---|
| 4,694,184 A * | 9/1987 | Pryor | ........................... | 33/551 |
| 4,876,758 A * | 10/1989 | Rolloff et al. | ................. | 33/551 |
| 4,914,827 A * | 4/1990 | Cook | ........................... | 33/552 |
| 4,916,824 A * | 4/1990 | Shimazutsu et al. | .......... | 33/551 |
| 5,001,841 A * | 3/1991 | Takigawa et al. | ............. | 33/551 |
| 5,198,877 A | 3/1993 | Schulz | | |
| 5,535,143 A * | 7/1996 | Face | ........................... | 33/551 |
| 5,640,779 A * | 6/1997 | Rolloff et al. | ............. | 33/514.2 |
| 5,883,313 A * | 3/1999 | Ercole et al. | .................. | 33/552 |
| 5,884,410 A * | 3/1999 | Prinz | ........................... | 33/559 |
| 6,029,077 A * | 2/2000 | Wake et al. | ................... | 33/555 |
| 6,160,264 A * | 12/2000 | Rebiere | ........................ | 33/552 |
| 6,236,875 B1 | 5/2001 | Bucholz et al. | | |
| 6,409,686 B1 | 6/2002 | Guthrie et al. | | |
| 6,427,353 B1 * | 8/2002 | Nelson et al. | ................. | 33/552 |
| 6,516,528 B1 * | 2/2003 | Choo et al. | .................... | 33/552 |
| 6,646,750 B1 * | 11/2003 | Christoph | ..................... | 33/559 |
| 6,701,633 B1 * | 3/2004 | Ohtsuka | ........................ | 33/552 |

(Continued)

FOREIGN PATENT DOCUMENTS

DE   198 51 153   9/2000

(Continued)

*Primary Examiner*—Yaritza Guadalupe
(74) *Attorney, Agent, or Firm*—Lipsitz & McAllister, LLC

(57) ABSTRACT

An apparatus for recording the contour of a surface of a body is provided in accordance with the present invention. The apparatus comprises a carrier on which at least one distance measuring element is disposed. The at least one distance measuring element is capable of determining a distance between the carrier and a location on the surface of the body. A navigation system with marking elements is provided. The marking elements are fixable on the carrier and on the body, such that positional data regarding the position of the body and the carrier can be determined by the navigation system. A data-processing device device is also provided, which is adapted to calculate the contour of the surface from the positional data of the body and of the carrier and the distance measurements of the at least one distance measuring element.

20 Claims, 2 Drawing Sheets

U.S. PATENT DOCUMENTS

| | | | |
|---|---|---|---|
| 6,848,191 B1 * | 2/2005 | Shiraishi et al. | 33/568 |
| 6,907,672 B1 * | 6/2005 | Said | 33/552 |
| 6,922,904 B1 * | 8/2005 | Groell et al. | 33/558 |
| 2004/0171929 A1 | 9/2004 | Leitner et al. | |

FOREIGN PATENT DOCUMENTS

| | | |
|---|---|---|
| DE | 101 05 822 | 8/2002 |
| EP | 0 944 237 | 9/1999 |

* cited by examiner

APPARATUS FOR RECORDING THE CONTOUR OF A SURFACE

This application is a continuation of international patent application no. PCT/EP2003/008856 filed on Aug. 8, 2003 and claims the benefit of German patent application no. 102 41 069.0 filed on Sep. 5, 2002, both of which applications are incorporated herein and made a part hereof by reference.

BACKGROUND OF THE INVENTION

The invention relates to an apparatus for recording the contour of a surface of a body.

Knowledge of the contour of irregular surfaces of a body, in particular the contour of depressions, is in many cases a prerequisite for being able to work on such a surface. For example, it is necessary in the case of an implantation of endoprostheses to know the exact shape of the surface of a bone structure in order accordingly to carry out an adaptation of implants, a necessary dressing of the bony structure or a suitable selection from various implants that are available.

SUMMARY OF THE INVENTION

It is an object of the invention to provide an apparatus of the generic type with which it is possible even in the case of irregular contours of the surface for this contour to be determined easily and reliably.

This object is achieved according to the invention in the case of an apparatus of the type described at the beginning by the apparatus comprising:

- a carrier on which at least one distance measuring element is disposed. The at leat one distance measuring element is capable of determining a distance between the carrier and a location on the surface of a body,
- a navigation system with marking elements which are fixable on the carrier and on the body, such that positional data reflecting the position of the body and the carrier can be determined by the navigation system, and
- a data-processing device, adapted to calculate the contour of the surface from positional data of the body and of the carrier and the distance measurements of the at least one distance measuring element.

Therefore, a carrier which assumes a determinable position in relation to the body and the specific surface is used, and on the carrier the distance of the surface from the carrier is determined by at least one distance measuring element. The data-processing device can determine the contour of the surface from the relative position of the carrier with respect to the body on the one hand and the distance of the surface from the carrier on the other hand if a measurement of this type is carried out at different locations of the surface.

In the simplest case, this can be achieved with a carrier with a single distance measuring element which is fixedly disposed on the carrier; in this case, the carrier with the distance measuring element is guided over the contour to be determined; in this way the contour is measured point by point and determined by the data-processing device.

This method is of course relatively laborious, and the accuracy also depends on how carefully the user moves the carrier over the entire surface to be recorded.

A significant improvement is obtained if, according to a preferred embodiment, a number of distance measuring elements are fixedly disposed on the carrier, distributed over a surface area, and their disposition on the carrier is stored in the data-processing device or continually transmitted to the latter. In this way, the distance measuring elements disposed on the carrier can simultaneously determine at various points of the surface their distance from the carrier, and the data-processing device can then determine the contour of the surface from the relative positioning of the distance measuring elements with respect to one another and from the individual measured distance values. If the number of distance measuring elements is sufficiently large and they cover the contour of the surface to be measured sufficiently completely, the contour can be calculated without movement of the carrier; it is therefore sufficient to position the carrier once with respect to the surface and then carry out a measurement, which immediately makes it possible to determine the contour of the entire surface.

However, it is also possible to move the carrier, which carries a number of distance measuring elements, relative to the surface for successive distance measurements, so that for each measurement the distance measuring elements are opposite a different region of the surface and carry out a distance measurement there. Since the position of the carrier in relation to the body is determined every time by the navigation system, it is also possible to associate the distance measurements with a specific location of the surface for every position of the carrier, so that the number of surface measuring points can be increased by means of measurements following one another in this way. It is in this way possible to use what may sometimes be a relatively small number of distance measuring elements to perform a determination of the contour of the surface nevertheless with great accuracy by means of a number of measurements following one another.

In the case of a further configuration, it is also possible for the distance measuring element to be able to move on the carrier into various positions and for data corresponding to the respective position of the distance measuring element on the carrier to be continually transmitted to the data-processing system.

In the case of this configuration, the surface is therefore traversed or scanned by the movable distance measuring element. In this case it is also possible for a number of movable distance measuring elements to be provided on such a carrier, which elements are displaced on the carrier simultaneously or one after the other. The displacement may be a physical displacement, but in principle it would also be possible in a relatively large gridwork of distance measuring elements to use them successively for carrying out measurements, so that the active measuring points and not the distance measuring elements themselves are moved along the carrier.

In all cases it is of significance that the user does not have to bring the carrier into a defined position with respect to the surface to be determined; it is sufficient if the position of the carrier is chosen such that the distance measuring elements can determine the distance from the surface; and even movements of the carrier during the distance measurements are not harmful, since these movements are recorded by the navigation system and can be taken into account by the data-processing system in the calculation of the contour of the surface.

According to a preferred embodiment, it is provided that the distance measuring element has a movable feeling element which can be placed on the surface and the different positions of which are recorded by a sensor and transmitted to the data-processing system. In the case of this type of distance determination, therefore, a contacting measurement is performed.

The feeling element may in this case be configured in a wide variety of ways; for example, the feeling element may be a longitudinally displaceable pin which is extended until it lies with its free end against the surface. Spherical elements which can be pushed to different extents into a guide on the carrier, pivotable feeling arms, etc., would also be conceivable.

The sensor for determining the position of the feeling element may likewise be configured in very different ways; for example, it may be an electrically operating sensor, in particular an electrical resistance measuring device, an electrical magnetic field measuring device, an electrical inductance or capacitance measuring device, or some other electrical measuring device which can determine the position of one body in relation to another.

It is also possible to use mechanical measuring devices, for example a pressure or strain measuring device. In other cases, an optical measuring device may be used; altogether, a person skilled in the art has many possibilities available to him for establishing the change in the position of the feeling element relative to the carrier.

In the case of another preferred embodiment, the distance is determined contactlessly. In particular, it may be provided in this case that the distance measuring element emits a radiation and receives the radiation reflected from the surface and that the distance between the distance measuring element and the surface is determined from the transit time of the radiation between emission and reception. This radiation may be, for example, an ultrasonic radiation or an electromagnetic radiation, in particular an infrared radiation or a laser radiation.

It is particularly advantageous if the carrier is in the form of a plate.

BRIEF DESCRIPTION OF THE DRAWINGS

The following description of preferred embodiments of the invention serves in connection with the drawing for a more detailed explanation. In the drawing.

DETAILED DESCRIPTION

Figure 1:
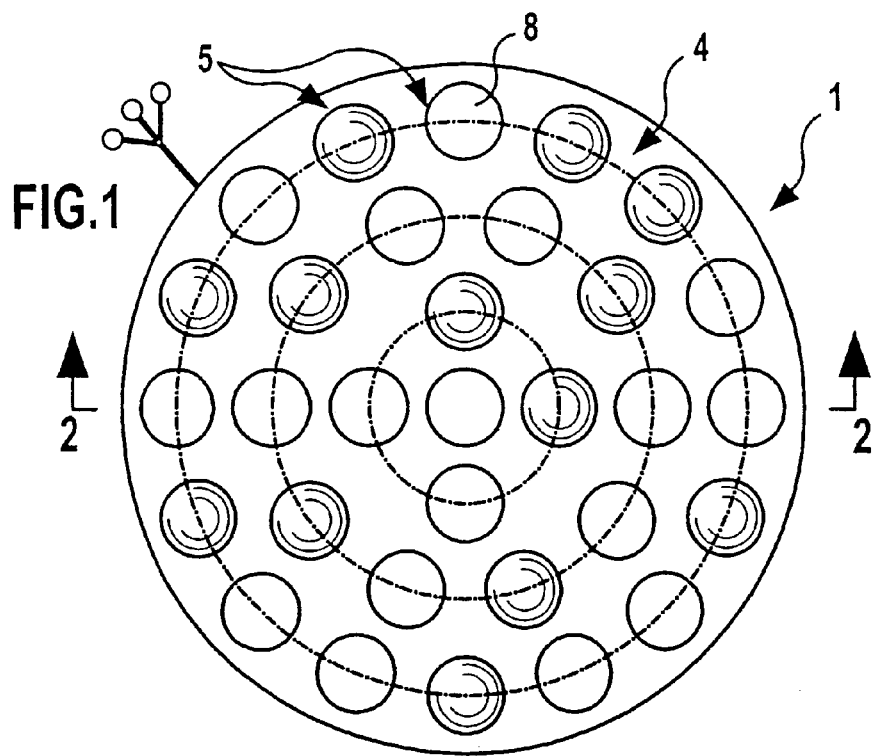
FIG. 1 shows a plan view of a contour recording apparatus with a multiplicity of distance measuring elements disposed on concentric circles.
Figure 2:
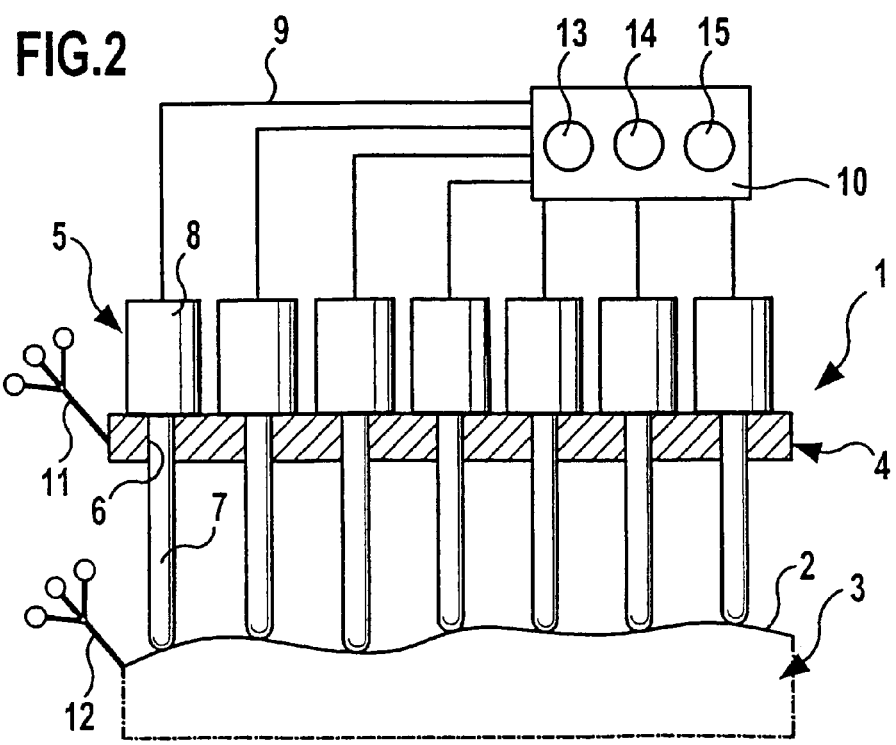
FIG. 2 shows a sectional view along line 2—2 in FIG. 1.

The apparatus 1 represented in FIGS. 1 and 2 serves for recording the contour of a surface 2 of any desired body, for example an bony structure 3. The apparatus 1 comprises carrier 4 in the form of a plate, which in the exemplary embodiment represented has a circular cross-section. Disposed on concentric circles with respect to the center point of the carrier 4 are a multiplicity of distance measuring elements 5, which respectively have a feeling pin 7, which protrudes through an opening 6 in the carrier 4 and is displaceable perpendicularly in relation to the extent of the carrier 4, and a sensor 8, which is fixedly disposed on the upper side of the carrier 4 and into which the feeling pin 7 can be pushed to a greater or lesser extent.

Each sensor 8 determines how far the feeling pin 7 is pushed into it; in other words, it therefore determines how far the feeling pin 7 protrudes downward out of the carrier 4. An electrical signal corresponding to this pushed-in depth is fed via a line 9 associated with each sensor 8 to a data-processing system 10, which in this way receives from all the sensors 8 data concerning how far the feeling pin 7 of the corresponding distance measuring element 5 has moved out downward from the carrier 4.

Fixed on the carrier 4 and on the bony structure 3 there is in each case a marking element 11 and 12, respectively; in a way known per se, this may comprise three spherical reflection elements for infrared radiation. A navigation system with three transmitting and receiving devices 13, 14, 15 is associated with the data-processing device 10. These transmitting and receiving devices emit for example infrared radiation, which is reflected at the marking elements 11, 12 and which is then received again by the transmitting and receiving devices 13, 14, 15. This navigation system can then determine from the differences in transit time the distance and the position of the two marking elements 11, 12 in relation to the navigation system, and consequently the spatial position and orientation both of the carrier 4 and of the bony structure 3. The navigation system supplies these positional data to the data-processing device 10.

If the carrier 4 is disposed next to the surface 2 of which the contour is to be determined, the feeling pins 7 are displaced by the force of gravity to the extent that they respectively lie against the surface 2, that is to say are moved out from the carrier 4 to different extents in a way corresponding to the contour of the surface 2, as can be gathered from the representation of FIG. 2. This position of the feeling pins 7 is established by the sensors 8 and passed on to the data-processing device 10, which can then calculate the contour of the surface 2 point by point from these data, the positional data of the distance measuring elements 5 on the carrier 4, which may be stored in a memory of the data-processing device 10, and the positional data of the carrier 4 and of the bony structure 3. On account of the multiplicity of distance measuring elements 5 on the carrier 4, a quite reliable picture of the contour of the surface 2 is obtained in this way. The accuracy can be improved by using a greater number of distance measuring elements 5, which are then brought closer together, or else by carrying out a number of such measurements one after the other, for which the carrier 4 is in each case displaced slightly in its position in relation to the surface 2. In this way, the feeling pins 7 come to lie against a different place on the surface 2 for each measurement and additional positional measurements of the surface structure are added to the previous measurements.

Figure 3:
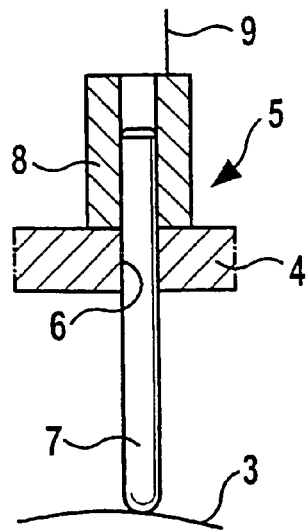
FIG. 3 shows a sectional view through a first preferred exemplary embodiment of a distance measuring element with a magnetic induction sensor.

The sensors may take very different forms; for example, represented in FIG. 3 is a distance measuring element 5 in the case of which the electrical properties of the sensor 8 surrounding the feeling pin 7 in the form of a sleeve are changed by the different pushed-in depth of the feeling pin 7, for example the inductance of a coil or the magnetic flux in a toroidal magnet, etc.

Figure 4:
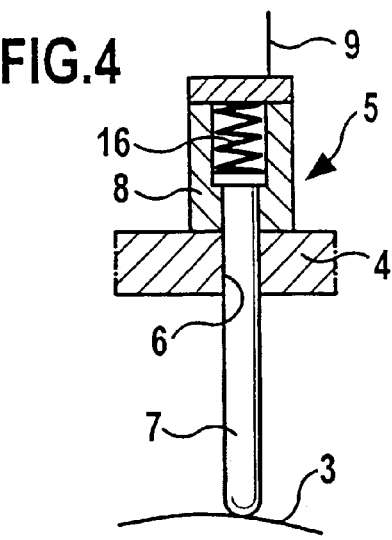
FIG. 4 shows a view similar to FIG. 3 with a pressure-sensitive sensor.

In the case of the exemplary embodiment of FIG. 4, the feeling pin 7 is pushed into the interior of the sensor 8 against a spring 16; the extension or compression of the spring can be determined by means of a strain gage, a pressure transducer or similar elements.

Figure 5:
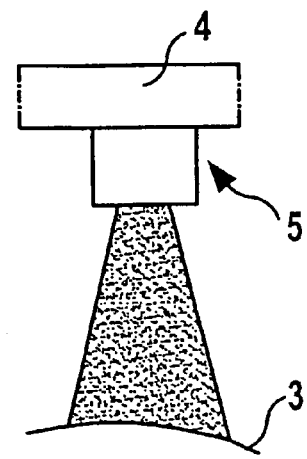
FIG. 5 shows a view similar to FIG. 3 with an ultrasonic distance measuring element.

In the case of the exemplary embodiment of FIG. 5, a contactless distance measuring element 5 which emits an ultrasonic radiation is schematically described. The sensor 8 receives the ultrasonic radiation reflected at the surface 2 and feeds a signal which represents the transit time of the ultrasonic radiation between emission and reception to the data-processing device 10. The distance of the surface 2 from the distance measuring element 5 can be determined from this transit time.

Figure 6:
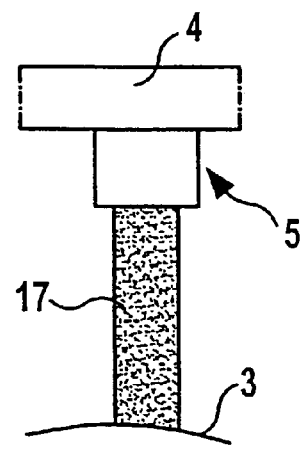
FIG. 6 shows a view similar to FIG. 5 with a laser-beam distance measuring element and FIG. 7 shows a schematic side view of a distance measuring element displaceably mounted on the carrier of the contour recording apparatus.

Instead of the ultrasonic radiation, an electromagnetic radiation may also be used, for example an infrared radiation or a laser radiation; in FIG. 6, a distance measuring element 5 which emits a laser beam 17 is represented.

Figure 7:
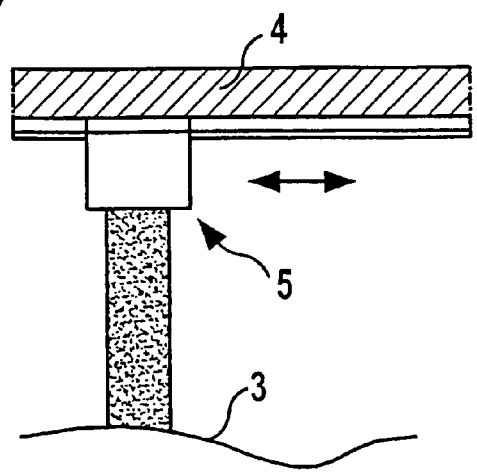

While in the case of the exemplary embodiments described so far the distance measuring elements 5 are fixedly disposed on the carrier 4, it would also be conceivable to mount one or more distance measuring elements 5 displaceably on the carrier 4, as is schematically represented in FIG. 7. The respective position of the distance measuring element 5 on the carrier 4 is then additionally determined by suitable sensors and likewise fed via a corresponding line to the data processing device 10, so that in different positions along the displacement path distance data and positional data of the distance measuring element 5 on the carrier 4 are processed in the data-processing device 10. It is consequently possible by means of the movable distance measuring element 5 to traverse the surface 2 and carry out distance measurements one after the other at different locations of this surface 2. In this case, such a movable distance measuring element 5 or else a number of such elements may be disposed on the carrier 4; in principle, it would also be possible to combine fixed distance measuring elements 5 with movable distance measuring elements 5 described in this way on a carrier 4.

What is claimed is:

1. Apparatus for recording the contour of a surface of a bone structure, comprising:
   a carrier,
   at least one distance measuring element disposed on the carrier for determining a distance between the carrier and a location on the surface of the bone structure,
   a navigation system with marking elements which are fixable on the carrier and on the bone structure, said marking elements adapted to communicate radiation to said navigation system to enable said navigation system to determine positional data indicative of the relative position of the bone structure with respect to the carrier, and
   a data-processing device adapted to calculate a contour of the surface from the positional data determined by the navigation system and distance measurements from the at least one distance measuring element.

2. Apparatus according to claim 1, wherein:
   a number of distance measuring elements are fixedly disposed on the carrier and distributed over a surface area, and
   said data-processing device is adapted to one of:
   (a) store dispositions of said distance measuring elements on said carrier; or
   (b) continually receive transmissions of said dispositions of said distance measuring elements on said carrier.

3. Apparatus according to claim 2, wherein said distance measuring elements comprise:
   a movable feeling element which can be placed on the surface, and
   a sensor adapted to record different positions of said movable feeling element and transmit said different positions to said data-processing system.

4. Apparatus according to claim 3, wherein said feeling element comprises a longitudinally displaceable pin.

5. Apparatus according to claim 2, wherein
   the distance measuring elements emit radiation and receive said radiation reflected from said surface, and
   said distance between said distance measuring elements and said surface is determined from a transit time of said radiation between emission and reception.

6. Apparatus according to claim 1, wherein
   said at least one distance measuring element is movable on the carrier into various positions, and
   data corresponding to said various positions of said at least one distance measuring element on said carrier is continually transmitted to the data-processing system.

7. Apparatus according to claim 6, wherein said at least one distance measuring element comprises:
   a movable feeling element which can be placed on the surface, and
   a sensor adapted to record different positions of said movable feeling element and transmit said different positions to said data-processing system.

8. Apparatus according to claim 6, wherein said feeling element comprises a longitudinally displaceable pin.

9. Apparatus according to claim 6, wherein
   the at least one distance measuring element emits radiation and receives said radiation reflected from said surface, and
   said distance between said at least one distance measuring element and said surface is determined from a transit time of said radiation between emission and reception.

10. Apparatus according to claim 1, wherein said at least one distance measuring element comprises:
    a movable feeling element which can be placed on the surface, and
    a sensor adapted to record different positions of said movable feeling element and transmit said different positions to said data-processing system.

11. Apparatus according to claim 10, wherein said feeling element comprises a longitudinally displaceable pin.

12. Apparatus according to claim 10, wherein said sensor comprises an electrical resistance measuring device.

13. Apparatus according to claim 10, wherein said sensor comprises a magnetic field measuring device.

14. Apparatus according to claim 10, wherein said sensor comprises one of an electrical inductance measuring device or capacitance measuring device.

15. Apparatus according to claim 10, wherein said sensor comprises one of a mechanical pressure device or a strain measuring device.

16. Apparatus according to claim 10, wherein said sensor comprises an optical measuring device.

17. Apparatus according to claim 1, wherein
    the at least one distance measuring element emits radiation and receives said radiation reflected from said surface, and
    said distance between said at least one distance measuring element and said surface is determined from a transit time of said radiation between emission and reception.

18. Apparatus according to claim 17, wherein said radiation comprises ultrasonic radiation.

19. Apparatus according to claim 17, wherein said radiation comprises electromagnetic radiation.

20. Apparatus according to claim 1, wherein said carrier comprises a plate.

* * * * *